US00PP29350P3

(12) United States Plant Patent
Wells

(10) Patent No.: US PP29,350 P3
(45) Date of Patent: May 29, 2018

(54) ***HELLEBORUS* PLANT NAMED 'MONOBYRN2'**

(50) Latin Name: *Helleborus hybrida*
Varietal Denomination: MONOBYRN2

(71) Applicant: Richard Wells, Dayton, OR (US)

(72) Inventor: Richard Wells, Dayton, OR (US)

(73) Assignee: Monrovia Nursery Co., Azusa, CA (US)

( * ) Notice: Subject to any disclaimer, the term of this patent is extended or adjusted under 35 U.S.C. 154(b) by 16 days.

(21) Appl. No.: 14/999,761

(22) Filed: Jun. 22, 2016

(65) Prior Publication Data

US 2017/0374789 P1 Dec. 28, 2017

(51) Int. Cl.
*A01H 5/02* (2018.01)

(52) U.S. Cl.
USPC ..... Plt./439
CPC ..... *A01H 5/02* (2013.01)

(58) Field of Classification Search
USPC ..... Plt./439
See application file for complete search history.

*Primary Examiner* — Susan McCormick Ewoldt
(74) *Attorney, Agent, or Firm* — Cassandra Bright

(57) ABSTRACT

A new and distinct *Helleborus* cultivar named 'MONOBYRN2' is disclosed, characterized by distinctive pure white sepals with vibrant red-purple veins. Flowers produce a double or triple row of sepals. The new cultivar is a *Helleborus*, suitable for ornamental garden purposes.

2 Drawing Sheets

Latin name of the genus and species: *Helleborus hybrida*. Variety denomination: 'MONOBYRN2'.

BACKGROUND OF THE INVENTION

The new cultivar was selected by the inventor, Richard Wells among a planting of seedling *Helleborus hybrida*. Seed and pollen parents are unidentified *Helleborus hybrida*. This new variety was discovered February 2012 as a single plant in a field of *Helleborus hybrida* seedlings in Salem, Oreg.

After identifying the new variety as a potentially interesting selection, the inventor first organized propagation of 'MONOBYRN2' by shoot tissue culture at a commercial laboratory in Oregon, during 2012. The inventor continued controlled testing and propagation, assessing stability of the unique characteristics of this variety. Several generations have been reproduced and have shown that the unique features of this cultivar are stable and reproduced true to type.

SUMMARY OF THE INVENTION

The cultivar 'MONOBYRN2' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MONOBYRN2' These characteristics in combination distinguish 'MONOBYRN2' as a new and distinct *Helleborus* cultivar:

1. Distinctive white flowers with pink picotee marginal coloring
2. Vibrant pink veins on both sides of sepals.
3. Double flowers.

COMPARISON TO PARENT VARIETY

The new variety is distinguished from unidentified parent variety by the unique large double and flower coloring of white with red-purple veins. No other varieties in the field of unnamed, unpatented *Helleborus hybrida* plants showed this unique coloring, together with a large double flower.

COMMERCIAL COMPARISON

'MONOBYRN2' can be compared to the commercial variety *Helleborus* 'Picotee Lady', unpatented. Plants of the new cultivar 'MONOBYRN2' are similar to plants of 'Picotee Lady' in most horticultural characteristics. Plants of the new cultivar 'MONOBYRN2' however, differ in the following:

1. The new variety produces a double whorl of sepals, this comparator produces a single whorl of sepals.
2. Sepal coloration of the new variety is more pure white, compared to the green-white sepal coloration of this comparator.
3. Stamen coloration of the new variety is cream colored, compared to yellow stamens of this comparator.

'MONOBYRN2' can be compared to the commercial variety *Helleborus* 'Double Ellen Picotee', unpatented. Plants of the new cultivar 'MONOBYRN2' are similar to plants of 'Double Ellen Picotee' in most horticultural characteristics. Plants of the new cultivar 'MONOBYRN2' however, differ in the following:

1. Mature sepal coloration of the new variety is white with pink venation. The comparator sepal coloration is white with Greyed-Purple or Greyed-Red venation.
2. Plants of the new variety are taller than plants of this comparator.

'MONOBYRN2' can be compared to the commercial variety *Helleborus* 'MONOBYRN1', co-pending, having application Ser. No. 14/999,762. Plants of the new cultivar 'MONOBYRN2' are similar to plants of 'MONOBYRN1' in most horticultural characteristics. Plants of the new cultivar 'MONOBYRN2' however, differ in the following:

1. Flowers of 'MONOBYRN1' have distinctive large, dark nectaries, 'MONOBYRN2' produces smaller nectaries of yellow-green flushed greyed-purple.
2. Flowers of 'MONOBYRN2' are double, plants of this comparator produce single flowers.

BRIEF DESCRIPTION OF THE PHOTOGRAPHS

The accompanying photographs illustrate the overall appearance of the new *Helleborus* 'MONOBYRN2' showing the colors as true as is reasonably possible with colored reproductions of this type. The figures depict flowers at various stages of maturity, on plants of approximately 18 months. Colors in the photographs may differ slightly from the color values cited in the detailed botanical description which accurately describes the color of 'MONOBYRN2'.

DETAILED BOTANICAL DESCRIPTION

Figure 1:
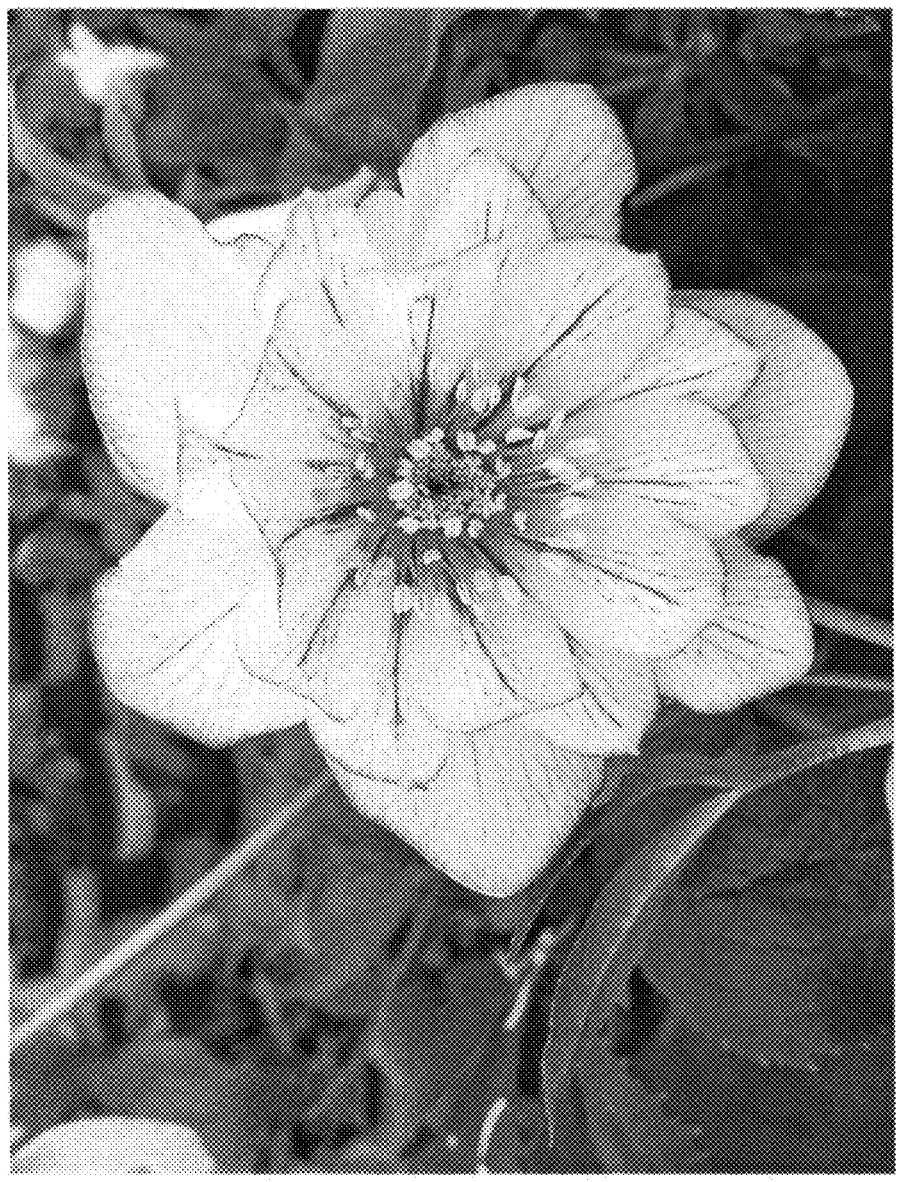
FIG. 1 shows a close-up of a mature flower.
Figure 2:
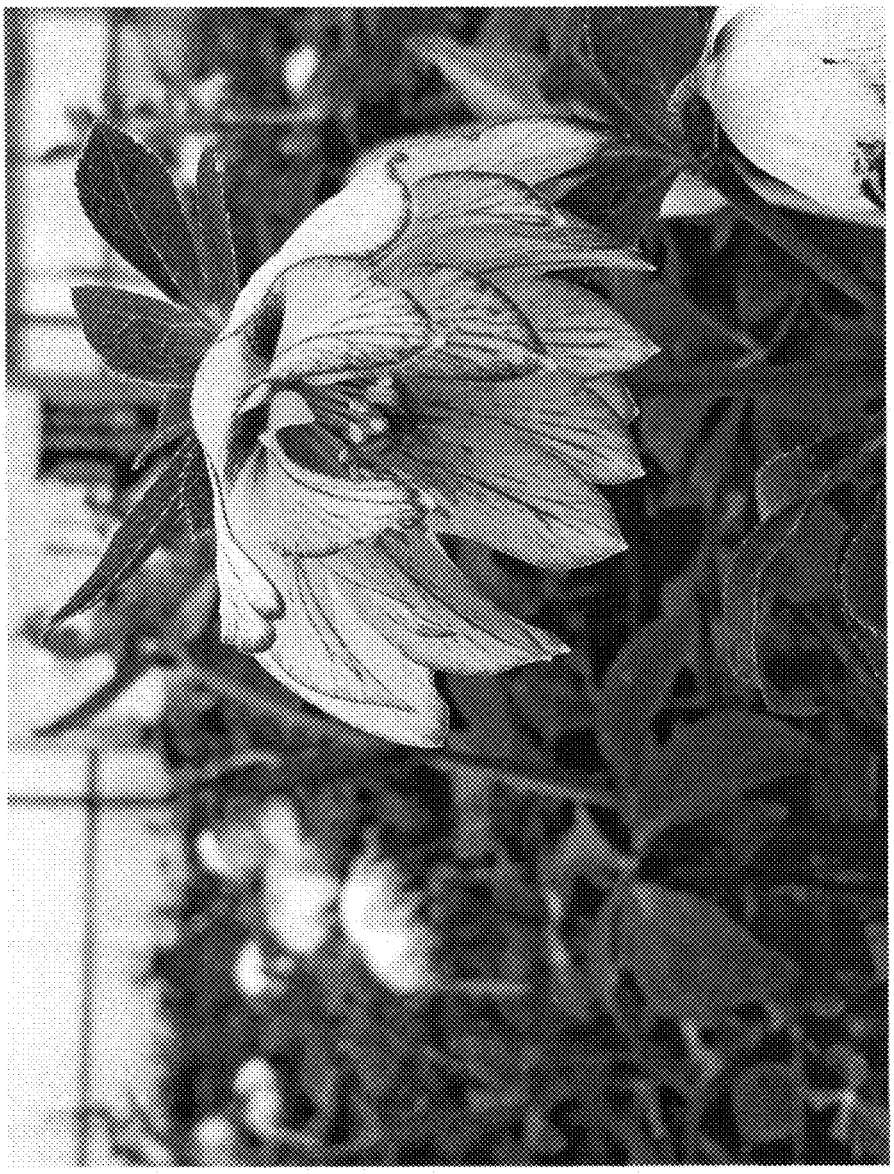
FIG. 2 depicts a mature flower seen from the reverse, showing the exterior of the sepals.

In the following description, color references are made to The Royal Horticultural Society Colour Chart 2007 except where general terms of ordinary dictionary significance are used. The following observations and measurements describe 'MONOBYRN2' plants grown outdoors in Salem Oreg. Plants are approximately 1 year old, in a 1 gallon nursery container. Measurements and numerical values represent averages of typical plant types.

Botanical classification: *Helleborus hybrida* 'MONOBYRN2'.

PROPAGATION

Typically by shoot tissue culture.

Root description: Single main root, moderate branching of short lateral roots. Cream to tan in color, not accurately measured with an R.H.S. chart.

PLANT

Growth habit: Moderate.

Height: Approximately 40 cm.

Plant spread: Approximately 40 cm.

Branching characteristics: No true branching. Leaves emerge direct from base of plant, or infrequently occur directly on the flowering stem.

Age of plant described: Approximately 1 year.

FOLIAGE

Leaf:

*Shape*.—Compound palmate.

*Quantity per stem*.—1.

*Length*.—11 to 14.0 cm.

*Diameter*.—15.0 cm.

*Quantity*.—Approximately 20 basal leaves, per plant.

Leaflets:

*Quantity*.—Average 5 to 7.

*Shape*.—Outermost leaflets elliptic. Center leaflets broadly elliptic to spatulate.

*Arrangement*.—Radial.

*Average length*.—Average 8.0 to 12.0 cm.

*Average width*.—Average 2.1 to 4.0 cm.

*Apex*.—Acute.

*Base*.—Attenuate.

*Margin*.—Sharply serrate.

*Texture of top surface*.—Glabrous.

*Texture of bottom surface*.—Glabrous.

*Appearance of top surface*.—Matte.

*Appearance of bottom surface*.—Matte.

*Aspect*.—Flat to very slightly reflexed downward.

*Color*.—Mature Leaflet: Upper side: Near RHS Green 137A. Under side: Near RHS Green 137C. Immature Leaflet: Upper side: Near RHS Green 137B. Under side: Near RHS Green 137D.

*Venation*.—Type: Palmate. Venation color upper side: Near RHS Yellow-Green 145A. Venation color under side: Center vein near RHS Yellow-Green N144A, lateral veins near Yellow-Green 147A. Foliage durability: Foliage has above average resistance to environmental stresses, including mechanical damage.

*Petiole*.—Length: Average range 18 to 25 cm. Diameter: 0.5 to 0.9 cm. Color: Near RHS Yellow-Green 145A. Texture: Pronounced ridges, glabrous. Aspect: Slightly arched.

*Stipules*.—Not observed.

FLOWER

Natural flowering season: Winter.

Inflorescence type and habit: Singly occurring radial flowers. Half dome shaped flower with upward curve. Typically flowers have a double whorl of sepals. Petals are modified into nectaries.

Flower longevity on plant: Approximately 2 weeks.

Quantity of flowers: Approximately 15 to 25, depending on environmental conditions, during peak flowering.

Flower size:

*Diameter*.—Approximately 6.5 cm.

*Height*.—Average range 3.7 cm.

Peduncle:

*Length*.—Approximately 5 to 15 cm.

*Diameter*.—Approximately 0.3 cm.

*Color*.—Near RHS Yellow-Green 144A.

*Strength*.—Moderately strong and very flexible.

*Texture*.—Glabrous.

*Aspect*.—Slightly undulating.

Bud:

*Shape*.—Spherical.

*Length*.—Approximately 3.0 cm.

*Diameter*.—Approximately 2.5 cm.

*Color*.—Near RHS Green-White 157A.

*Rate of opening*.—Approximately 3 to 7 days from color flushed bud to open flower.

Sepals:

*Quantity*.—Typically 18, 6 large outer sepals, 12 smaller inner.

*Length*.—Outer/Large: 4.0 cm Inner/Small: 2.7 to 3.2 cm.

*Width*.—Outer/Large: 2.4 cm Inner/Small: 0.8 cm.

*Shape*.—Outer sepals broad elliptic, inner sepals elliptic.

*Aspect*.—Upwardly cupped.

*Apex*.—Acute.

*Base*.—Attenuate.

*Margin*.—Entire, ruffled.

*Color*.—When opening: Interior Surface: Near RHS Green-White 157D, veins near Red-Purple 70A.

Exterior Surface: Near RHS Green-White 157D, veins near Red-Purple 70A. Mature: Interior Surface: Near White N155A, veins and margin near Red-Purple 70A. Exterior Surface: Near White N155A, veins and margin near Red-Purple 70A. Flushing near apex 70A. Aging: Interior Surface: Near White N155A, veins and margin near Red-Purple 70A. Flushing near apex 70A. Exterior Surface: Near White N155A, veins and margin near Red-Purple 70A. Flushing near apex 70A.

Nectaries (modified petals):

*Quantity*.—Average 4 to 6.

*Shape*.—Tubular.

*Length*.—Approximately 0.4 cm.

*Diameter*.—Approximately 0.2 cm.

*Color*.—Near RHS Yellow-Green 144A, flushed Greyed-Purple N186A.

*Texture*.—Glabrous.

Fragrance: None detected.

REPRODUCTIVE ORGANS

Stamens:

*Number*.—Approximately 30 per flower.

*Filament length*.—Approximately 0.4 cm.

*Filament color*.—Near RHS Green-White 157C.

Anthers:

*Length*.—0.1 cm.

*Shape*.—Linear.

*Color*.—Near RHS Yellow-White 158D.

*Pollen*.—Amount: Scant. Color: Near RHS Yellow-White 158D.

Pistil:

*Number*.—Typically 4 to 6 per flower.

*Length*.—Approximately 0.7 cm.

*Style color*.—Near RHS Green-White 157C.

*Style length*.—Approximately 0.4 cm.

*Stigma*.—Shape: Club shape. Color: Near RHS Greyed-Purple N186A.

*Ovary*.—Near RHS Yellow-Green 144C.

OTHER CHARACTERISTICS

Disease and pest resistance: Not observed to be susceptible nor resistant to normal diseases and pests of *Helleborus* Typical pests include Aphid and Thrips. The most common fungal disease is *Coniotyrium hellebore*. The Genus is also known to suffer from various Nematodes, as well as *Pythium, Phytophtora* and *Rhizoctonia*.

Temperature tolerance: Typically USDA Zones 3 to 9.

Fruit/seed production: Not observed.

What is claimed is:

1. A new and distinct cultivar of *Helleborus* plant named 'MONOBYRN2' as herein illustrated and described.

* * * * *